US011400132B2

(12) United States Patent
Löscher et al.

(10) Patent No.: US 11,400,132 B2
(45) Date of Patent: *Aug. 2, 2022

(54) OPHTHALMIC COMPOSITIONS COMPRISING CICLOSPORIN

(71) Applicant: NOVALIQ GMBH, Heidelberg (DE)

(72) Inventors: Frank Löscher, Schriesheim (DE); Ralf Grillenberger, Ilvesheim (DE); Johan Engblom, Lund (SE)

(73) Assignee: NOVALIQ GMBH, Heidelberg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 17/069,417

(22) Filed: Oct. 13, 2020

(65) Prior Publication Data

US 2021/0023166 A1    Jan. 28, 2021

Related U.S. Application Data (63) Continuation of application No. 16/336,005, filed as application No. PCT/EP2017/074079 on Sep. 22, 2017, now Pat. No. 10,813,976.

(30) Foreign Application Priority Data

Sep. 23, 2016  (EP) .................................. 16190431.3

(51) Int. Cl.
| | | |
|---|---|---|
| A61K 38/13 | (2006.01) | |
| A61K 9/00 | (2006.01) | |
| A61K 9/08 | (2006.01) | |
| A61K 47/06 | (2006.01) | |

(52) U.S. Cl.
CPC ............ *A61K 38/13* (2013.01); *A61K 9/0048* (2013.01); *A61K 9/08* (2013.01); *A61K 47/06* (2013.01)

(58) Field of Classification Search
None
See application file for complete search history.

(56) References Cited

U.S. PATENT DOCUMENTS

| | | |
|---|---|---|
| 2,616,927 A | 11/1952 | Kauck et al. |
| 5,077,036 A | 12/1991 | Long, Jr. |
| 5,152,997 A | 10/1992 | Elbert et al. |
| 5,254,338 A | 10/1993 | Sakai et al. |
| 5,326,566 A | 7/1994 | Parab |
| 5,336,175 A | 8/1994 | Mames |
| 5,370,313 A | 12/1994 | Beard |
| 5,518,731 A | 5/1996 | Meadows |
| 5,667,809 A | 9/1997 | Trevino |
| 5,851,544 A | 12/1998 | Penska et al. |
| 5,874,469 A | 2/1999 | Maniar et al. |
| 5,874,481 A | 2/1999 | Weers |
| 5,980,936 A | 11/1999 | Krafft et al. |
| 5,981,607 A | 11/1999 | Ding |
| 6,042,845 A | 3/2000 | Sun et al. |
| 6,060,085 A | 5/2000 | Osborne |
| 6,113,919 A | 9/2000 | Cronelus |
| 6,159,977 A | 12/2000 | Reeves |
| 6,177,477 B1 | 1/2001 | George et al. |
| 6,197,323 B1 | 3/2001 | Georgieff |
| 6,224,887 B1 | 5/2001 | Samour et al. |
| 6,262,126 B1 | 7/2001 | Meinert |
| 6,294,563 B1 | 9/2001 | Garst |
| 6,372,243 B2 | 4/2002 | Kobuch et al. |
| 6,391,879 B1 | 5/2002 | Reeves |
| 6,458,376 B1 | 10/2002 | Meadows |
| 6,486,212 B2 | 11/2002 | Meinert |
| 6,489,367 B1 | 12/2002 | Meinert |
| 6,528,086 B2 | 3/2003 | Zhang |
| 6,730,328 B2 | 5/2004 | Maskiewicz |
| 7,001,607 B1 | 2/2006 | Menz |
| 7,026,359 B1 | 4/2006 | Gross |
| 7,258,869 B1 | 8/2007 | Berry |
| 7,740,875 B2 | 6/2010 | Dechow |
| 8,029,977 B2 | 10/2011 | Meinert et al. |
| 8,222,292 B2 | 7/2012 | Goskonda et al. |
| 8,470,873 B2 | 6/2013 | Chen |
| 8,614,178 B2 | 12/2013 | Theisinger et al. |
| 8,796,340 B2 | 8/2014 | Theisinger et al. |
| 8,916,157 B2 | 12/2014 | Krause et al. |
| 8,986,738 B2 | 3/2015 | Meinert |
| 9,241,900 B2 | 1/2016 | Wilson |
| 9,308,262 B2 | 4/2016 | Wilson |
| 9,757,459 B2 | 9/2017 | Theisinger et al. |
| 9,757,460 B2 | 9/2017 | Günther et al. |
| 9,770,508 B2 | 9/2017 | Günther et al. |
| 9,968,678 B2 | 5/2018 | Theisinger et al. |

(Continued)

FOREIGN PATENT DOCUMENTS

| | | |
|---|---|---|
| CN | 1147213 A | 4/1997 |
| CN | 200977281 | 11/2007 |

(Continued)

OTHER PUBLICATIONS

Ahmed, et al., "Disposition of Timolol and Inulin in the Rabbit Eye Following Corneal Versus Non-Corneal Absorption," International Journal of Pharmaceutics, 1987, 38:9-21.

Baerdemaeker, "Pharmacokinetics in Obese Patients," Continuing Education in Anesthesia, Critical Care & Pain, 2004, 4:152-155.

Barata-Vallejo et al., "(Me₃Si)₃SiH-Mediated Intermolecular Radical Perfluoroalkylation Reactions of Olefins in Water," J. Org. Chem., 2010, 75:6141-6148.

Bardin et al., "Long-Range Nanometer-Scale Organization of Semifluorinated Alkane Monolayers at the Air/Water Interface," Langmuir, 2011, 27:13497-13505.

(Continued)

*Primary Examiner* — Christina Bradley (74) *Attorney, Agent, or Firm* — Hoxie & Associates LLC (57) ABSTRACT

The present invention relates to compositions in the form of a clear solution comprising ciclosporin with low residual water content and 1-perfluorobutyl-pentane. The compositions may be used for topical administration to the eye.

14 Claims, 2 Drawing Sheets

(56) References Cited

U.S. PATENT DOCUMENTS

| | | |
|---|---|---|
| 10,045,996 B2 | 8/2018 | Theisinger et al. |
| 10,058,615 B2 | 8/2018 | Günther et al. |
| 10,064,944 B2 | 9/2018 | Wilson |
| 10,130,707 B2 | 11/2018 | Gunther et al. |
| 10,273,298 B2 | 4/2019 | Günther et al. |
| 10,369,117 B2 | 8/2019 | Günther et al. |
| 10,449,164 B2 | 10/2019 | Günther et al. |
| 10,507,132 B2 | 12/2019 | Graf et al. |
| 10,525,062 B2 | 1/2020 | Theisinger et al. |
| 10,555,953 B2 | 2/2020 | Theisinger et al. |
| 10,576,154 B2 | 3/2020 | Günther et al. |
| 10,682,315 B2 | 6/2020 | Scherer et al. |
| 10,813,976 B2 * | 10/2020 | Loscher ............... A61K 47/06 |
| 10,813,999 B2 | 10/2020 | Günther et al. |
| 11,154,513 B2 | 10/2021 | Scherer et al. |
| 11,160,865 B2 | 11/2021 | Theisinger et al. |
| 2002/0004063 A1 | 1/2002 | Zhang |
| 2002/0128527 A1 | 9/2002 | Meinert |
| 2003/0018044 A1 | 1/2003 | Peyman |
| 2003/0027833 A1 | 2/2003 | Cleary et al. |
| 2003/0170194 A1 | 11/2003 | Piotrowiak |
| 2004/0044045 A1 | 3/2004 | Burk |
| 2004/0082660 A1 | 4/2004 | Ueno |
| 2004/0101551 A1 | 5/2004 | Selzer |
| 2004/0265362 A1 | 12/2004 | Susilo |
| 2004/0266702 A1 | 12/2004 | Dawson |
| 2005/0075407 A1 | 4/2005 | Dov et al. |
| 2005/0079210 A1 | 4/2005 | Gupta |
| 2005/0175541 A1 | 8/2005 | Lanza et al. |
| 2005/0274744 A1 | 12/2005 | Spada et al. |
| 2005/0288196 A1 | 12/2005 | Horn |
| 2006/0153905 A1 | 7/2006 | Carrara et al. |
| 2008/0050335 A1 | 2/2008 | Faour et al. |
| 2008/0153909 A1 | 6/2008 | Dana et al. |
| 2008/0207537 A1 | 8/2008 | Turner et al. |
| 2008/0234389 A1 | 9/2008 | Mecozzi et al. |
| 2008/0260656 A1 | 10/2008 | Mallard |
| 2009/0136430 A1 | 5/2009 | Dugger |
| 2009/0149546 A1 | 6/2009 | Chang |
| 2009/0169601 A1 | 7/2009 | Koch et al. |
| 2010/0006600 A1 | 1/2010 | Dascanio |
| 2010/0008996 A1 | 1/2010 | Meinert |
| 2010/0016814 A1 | 1/2010 | Gokhale et al. |
| 2010/0226997 A1 | 9/2010 | Bowman et al. |
| 2010/0274215 A1 | 10/2010 | Wong et al. |
| 2010/0310476 A1 | 12/2010 | Tamarkin et al. |
| 2011/0269704 A1 | 11/2011 | Seigfried |
| 2012/0010280 A1 | 1/2012 | Aleo et al. |
| 2012/0095097 A1 | 4/2012 | Tabuchi et al. |
| 2012/0238639 A1 | 9/2012 | Theisinger et al. |
| 2012/0244177 A1 | 9/2012 | Theisinger |
| 2013/0046014 A1 | 2/2013 | Theisinger et al. |
| 2013/0084250 A1 | 4/2013 | Hagedorn et al. |
| 2013/0266652 A1 | 10/2013 | Theisinger et al. |
| 2013/0303473 A1 | 11/2013 | Wilson |
| 2013/0336557 A1 | 12/2013 | Cruzat et al. |
| 2014/0004197 A1 | 1/2014 | Theisinger et al. |
| 2014/0100180 A1 | 4/2014 | Günther et al. |
| 2014/0140942 A1 | 5/2014 | Günther et al. |
| 2014/0186350 A1 | 7/2014 | Ghosh et al. |
| 2014/0369993 A1 | 12/2014 | Günther et al. |
| 2015/0045282 A1 | 2/2015 | Elsohly et al. |
| 2015/0224064 A1 | 8/2015 | Günther et al. |
| 2015/0238605 A1 | 8/2015 | Günther et al. |
| 2016/0000941 A1 | 1/2016 | Thorsten et al. |
| 2016/0101178 A1 | 4/2016 | Wilson |
| 2016/0159902 A1 | 6/2016 | Günther et al. |
| 2016/0243189 A1 | 8/2016 | Gu et al. |
| 2017/0020726 A1 | 1/2017 | Labombarbe et al. |
| 2017/0087100 A1 | 3/2017 | Scherer et al. |
| 2017/0087101 A1 | 3/2017 | Scherer et al. |
| 2017/0182060 A1 | 6/2017 | Wiedersberg et al. |
| 2018/0360908 A1 | 12/2018 | Beier et al. |
| 2019/0274970 A1 | 9/2019 | Günther et al. |
| 2019/0328717 A1 | 10/2019 | Günther et al. |
| 2019/0343793 A1 | 11/2019 | Günther et al. |
| 2020/0060987 A1 | 2/2020 | Günther et al. |
| 2020/0129543 A1 | 4/2020 | Löscher et al. |
| 2020/0188318 A1 | 6/2020 | Günther et al. |
| 2020/0206241 A1 | 7/2020 | Theisinger et al. |
| 2020/0246463 A1 | 8/2020 | Günther et al. |
| 2020/0268648 A1 | 8/2020 | Günther et al. |
| 2020/0268682 A1 | 8/2020 | Günther et al. |
| 2020/0338015 A1 | 10/2020 | Scherer et al. |
| 2020/0360285 A1 | 11/2020 | Theisinger et al. |
| 2021/0069014 A1 | 3/2021 | Löscher et al. |
| 2021/0100904 A1 | 4/2021 | Günther et al. |
| 2021/0106558 A1 | 4/2021 | Löscher et al. |
| 2021/0121471 A1 | 4/2021 | Löscher et al. |
| 2021/0228595 A1 | 7/2021 | Löscher et al. |
| 2021/0236591 A1 | 8/2021 | Leo et al. |
| 2021/0315832 A1 | 10/2021 | Scherer et al. |
| 2021/0340248 A1 | 11/2021 | Günther et al. |
| 2021/0346313 A1 | 11/2021 | Beier et al. |
| 2022/0008397 A1 | 1/2022 | Xu et al. |

FOREIGN PATENT DOCUMENTS

| | | |
|---|---|---|
| CN | 202136470 U | 2/2012 |
| CN | 203524843 U | 4/2014 |
| EP | 0 089 815 | 9/1983 |
| EP | 0593552 | 4/1994 |
| EP | 0 670 159 | 9/1995 |
| EP | 0 965 329 | 12/1999 |
| EP | 0 965 334 | 12/1999 |
| EP | 1 152 749 | 11/2001 |
| EP | 0 939 655 | 6/2002 |
| EP | 2 110 126 | 10/2009 |
| EP | 2 332 525 | 6/2011 |
| EP | 2 335 735 | 6/2011 |
| EP | 2 462 921 | 6/2012 |
| JP | S6452722 | 2/1989 |
| JP | 2000511157 | 8/2000 |
| JP | 2001/158734 | 6/2001 |
| JP | 2008/505177 | 2/2008 |
| JP | 2011/006348 | 1/2011 |
| JP | 2011/024841 A | 2/2011 |
| WO | WO 92/10231 | 6/1992 |
| WO | WO 1995/033447 | 12/1995 |
| WO | WO 96/40052 | 12/1996 |
| WO | WO 97/12852 | 4/1997 |
| WO | WO 1998/005301 | 12/1998 |
| WO | WO 00/10531 | 3/2000 |
| WO | WO 00/024376 | 5/2000 |
| WO | WO 00/054588 | 9/2000 |
| WO | WO 2002/49631 A1 | 6/2002 |
| WO | WO 2003/099258 | 12/2003 |
| WO | WO 2005/018530 | 3/2005 |
| WO | WO 2005/099718 | 10/2005 |
| WO | WO 2005/099752 | 10/2005 |
| WO | WO 2005/123035 | 12/2005 |
| WO | WO 2006/007510 | 1/2006 |
| WO | WO 2006/042059 | 4/2006 |
| WO | WO 2006/048242 | 5/2006 |
| WO | WO 2007/052288 | 5/2007 |
| WO | WO 2008/019146 | 2/2008 |
| WO | WO 2008/060359 | 5/2008 |
| WO | WO 2009/013435 | 1/2009 |
| WO | WO 2009/065565 | 5/2009 |
| WO | WO 2010/062394 | 6/2010 |
| WO | WO 2010/146536 | 12/2010 |
| WO | WO 2011/009436 | 1/2011 |
| WO | WO 2011/073134 | 6/2011 |
| WO | WO 2011/113855 | 9/2011 |
| WO | WO 2012/052418 | 4/2012 |
| WO | WO 2012/062834 | 5/2012 |
| WO | WO 2012/093113 | 7/2012 |
| WO | WO 2012/121754 | 9/2012 |
| WO | WO 2012/160179 | 11/2012 |
| WO | WO 2012/160180 | 11/2012 |
| WO | WO 2013/110621 | 8/2013 |
| WO | WO 2014/041055 | 3/2014 |
| WO | WO 2014/041071 | 3/2014 |
| WO | WO 2014/154531 | 10/2014 |

(56) References Cited

FOREIGN PATENT DOCUMENTS

| WO | WO 2015/011199 | 1/2015 |
|---|---|---|
| WO | WO 2015/053829 | 4/2015 |
| WO | WO 2015/074137 | 5/2015 |
| WO | WO 2016/025560 | 2/2016 |
| WO | WO 2016/109531 | 7/2016 |
| WO | WO 2017/220625 | 12/2017 |
| WO | WO 2018/054932 | 3/2018 |
| WO | WO 2018/060282 | 4/2018 |
| WO | WO 2018/114557 | 6/2018 |
| WO | WO 2018/115097 | 6/2018 |

OTHER PUBLICATIONS

Bertilla et al., "Semifluorinated Alkanes as Stabilizing Agents of Fluorocarbon Emulsions," Springer, Tokyo, 2005, International Symposia for Life Sciences and Medicine, vol. 12, pp. 237-251.
Blackie et al., "MGD: Getting to the Root Cause of Dry Eye," Review of Optometry, 2012, pp. 1-12.
Broniatowski, M. et al., "Langmuir Monolayers Characteristics of (Perfluorodecyl)-Alkanes," Journal of Physical Chemistry B, 2004, 108:13403-13411.
Chemical Book, 5-Fluorouracil, available at <http://www.chemicalbook.com/ChemicalProductProperty_EN_CB8162744.htm>, accessed Mar. 7, 2014, 1 page.
Chhadva et al., "Meibomian Gland Disease The Role of Gland Dysfunction in Drye Eye Disease," Ophthalmology (2017) 124(11 Supplement): S20-S26.
Costa Gomes et al., "Solubility of dioxygen in seven fluorinated liquids," Journal of Fluorine Chemistry, 2004, 125:1325-1329.
Davies, "Biopharmaceutical Considerations in Topical Ocular Drug Delivery," Clin. Exper. Pharmacol. Physiol., 2000, 27:558-562.
Dembinski et al., Semi-fluorinated Alkanes as Carriers for Drug Targeting in Acute Respiratory Failure, Experimental Lung Research, 2010, 36(8):499-507.
Dias et al., "Solubility of oxygen in liquid perfluorocarbons," Fluid Phase Equilibria, 2004, 222-223:325-330.
Dutescu et al., "Semifluorinated alkanes as a liquid drug carrier system for topical ocular drug delivery," European Journal of Pharmaceutics and Biopharmaceutics, 2014, 88(1):123-128, Abstract Only (2 pages).
Elkeeb, R. et al., "Transungual Drug Delivery: Current Status," International Journal of Pharmaceutics, 2010, 384:1-8.
English-language machine translation of EP0670159 (A1) issued in U.S. Appl. No. 14/122,025, filed Apr. 1, 2015, 10 pages.
Freiburger Dokumentenserver (FreiDok), Albert-Ludwigs, Unversitat Feiburg im Breisgau, retrieved from the Internet, date accessed: Feb. 5, 2014, 2 pages URL: <http://www.freidok.uni-freiburg.de/volltexte/5682>.
Gayton, J., "Etiology, Prevalence, and Treatment of Dry Eye Disease," Clinical Ophthalmology, 2009, 3:405-412.
Gehlsen et al., "A semifluorinated alkane (F4H5) as novel carrier for cyclosporine A: a promising therapeutic and prophylactic option for topical treatment of dry eye," Graefe's Arch. Clin. Exp. Ophthalmol., (2017) 255(4):767-775.
Gehlsen. U., et al., "Cyclosporine A using F4H5 as liquid drug carrier is effective in treating experimental dry-eye disease," Investigative Ophthalmology & Visual Science, 2015, 56(7):319, Abstract Only (2 pages).
Gerdenitsch, "Emulsions—established and promising drug carriers for parenteral administration," retrieved from Internet, date accessed: Jun. 20, 2016, 2 pages URL: <http:/ipimediaworld.com/wp-content/uploads/2012/05/Pages-from-IPI-Volume-2-Issue-1-11.pdf.>.
Gopal et al., "Use of intravitreal injection of triamcinolone acetonide in the treatment of age-related macular degeneration," Indian J Ophthalmol., 2007, 55(6):431-435, (8 pages).
Griffin, W., "Classification of Surface-Active Agnets by 'HLB'," Journal Of The Society of Cosmetic Chemists,1949, 1:311-326.
Hardung, H., "Semifluorierte und perfluorierte Vergindungen zur topischen und parenteralen Anwendung," 2008, 188 pages, retrieved from Internet, date accessed: Oct. 10, 2011, URL: <http://www.freidok.uni-freiburg.de/volltexte/5682/pdf/Dissertation_Hardung.pdf>.
Hardung, H., "Semifluorierte und perfluorierte Verbindungen zur topischen und parenteralen Anwendung," 2008, English Language Abstract, 2 pages, retrieved from https://freidok.uni-freiburg.de/data/5682 (retrieved on Jul. 10, 2017).
Hoerauf et al., "Combined Use of Partially Fluorinated Alkanes, Perfluorocarbon Liquids and Silicone Oil: An Experimental Study," Graefe's Archive For Clinical And Experimental Ophthalmology, 2001, 239(5):373-381.
Holm, R. et al., "A novel excipient, 1-perfluorohexyloctane shows limited utility for the oral delivery of poorly water-soluble drugs," European Journal of Pharmaceutical Sciences, 2011, 42: 416-422.
International Preliminary Report on Patentability dated Apr. 23, 2013, for International Patent Application PCT/EP2011/068141, 4 Pages.
International Preliminary Report on Patentability dated Sep. 18, 2012, for International Patent Application PCT/EP2011/053949, 9 Pages.
International Preliminary Report on Patentability dated May 14, 2013, for International Patent Application PCT/EP2011/069795, 8 Pages.
International Preliminary Report on Patentability dated Jul. 10, 2013, for International Patent Application PCT/EP2012/050043, 5 Pages.
International Preliminary Report on Patentability dated Nov. 26, 2013, for International Patent Application PCT/EP2012/059787, 9 Pages.
International Preliminary Report on Patentability dated Nov. 26, 2013, for International Patent Application PCT/EP2012/059788, 8 Pages.
International Preliminary Report on Patentability dated Jul. 29, 2014, for International Application No. PCT/EP2013/051163, 7 pages.
International Preliminary Report on Patentability dated Mar. 17, 2015, for International Application No. PCT/EP2013/068882, 5 pages.
International Preliminary Report on Patentability dated Mar. 17, 2015, for International Application No. PCT/EP2013/068909, 7 pages.
International Preliminary Report on Patentability dated Dec. 25, 2018, for International Application No. PCT/EP2017/065163, 6 pages.
International Preliminary Report on Patentability dated Jan. 26, 2016, for International Application No. PCT/EP2014/065840, 11 pages.
International Preliminary Report on Patentability dated Mar. 26, 2019, for International Application No. PCT/EP2017/073697, 7 pages.
International Preliminary Report on Patentability dated Mar. 26, 2019, for International Application No. PCT/EP2017/074079, 7 pages.
International Preliminary Report on Patentability dated Apr. 2, 2019, for International Application No. PCT/EP2017/074545, 7 pages.
International Preliminary Report on Patentability dated Jun. 25, 2019, for International Application No. PCT/EP2017/082739, 7 pages.
International Search Report for International Application No. PCT/EP2011/053949 dated Sep. 6, 2011, 5 pages.
International Search Report for International Application No. PCT/EP2011/068141 dated Dec. 14, 2011, 2 pages.
International Search Report for International Patent Application PCT/EP2011/069795 dated Jan. 16, 2012, 3 pages.
International Search Report for International Patent Application PCT/EP2012/050043 dated Apr. 24, 2012, 2 pages.
International Search Report for International Application No. PCT/EP2012/059787 dated Dec. 5, 2012, 4 pages.
International Search Report for International Application No. PCT/EP2012/059788 dated Dec. 3, 2012, 4 pages.
International Search Report for International Application No. PCT/EP2013/051163 dated Mar. 4, 2013, 4 pages.

(56) References Cited

OTHER PUBLICATIONS

International Search Report for International Application No. PCT/EP2013/068882 dated Oct. 30, 2013, 4 pages.
International Search Report for International Application No. PCT/EP2013/068909 dated Dec. 5, 2013, 4 pages.
International Search Report for International Application No. PCT/EP2014/065840 dated Oct. 7, 2014, 4 pages.
International Search Report for International Application No. PCT/EP2016/073262 dated Nov. 18, 2016, 5 pages.
International Search Report for International Application No. PCT/EP2016/073263 dated Dec. 23, 2016, 3 pages.
International Search Report for International Application No. PCT/EP2017/065163, dated Aug. 8, 2017, 3 pages.
International Search Report for International Application No. PCT/EP2017/073697 dated Nov. 6, 2017, 4 pages.
International Search Report for International Application No. PCT/EP2017/074079 dated Dec. 22, 2017, 4 pages.
International Search Report for International Application No. PCT/EP2017/074545 dated Nov. 28, 2017, 3 pages.
International Search Report for International Application No. PCT/EP2017/082739 dated Mar. 6, 2018, 3 pages.
International Search Report for International Application No. PCT/EP2017/083770 (revised version) dated Jul. 6, 2018, 4 pages.
International Search Report and Written Opinion for International Application No. PCT/EP2017/083770 dated Jul. 6, 2018, 14 pages.
Ishizaki et al., "Treatment of Diabetic Retinopathy," Forum: Complication, Practice, 2009, 26(5): 474-476 (3 pages).
Jonas et al., "Intravitreal triamcinolone acetonide for exudative age-related macular degeneration," Br J Ophthalmol, 2003, 87:462-468.
Joussen et al., "The concept of heavy tamponades—chances and limitations," Graefes Arch Exp Ophthalmol, 2008, 246:1217-1224.
JP 2000511157A, English Machine Translation of the Abstract, Description, and Claims, Espacenet, Date Accessed: Feb. 10, 2016, 15 pages.
JPS6452722, English Machine Translation of the Abstract, Description, and Claims, Espacenet, Date Accessed: Feb. 10, 2016, 4 pages.
Kaercher et al., "NovaTears® as new Therapy in Dry Eye Results from three prospective, multicenter, non-interventional studies in different patient populations," TFOS Conference (Tear Film & Ocular Surface), Sep. 7-10, 2016, Montpellier, France, Poster Session II, Poster No. 60, 1 page.
Knepp et al., "Stability of Nonaqueous Suspension Formulations of Plasma Derived Factor IX and Recombinant Human Alpha Interferon at Elevated Temperatures," Pharmaceutical Research, 1998, 15 (7):1090-1095.
Kociok, N., "Influence on Membrane-Mediated Cell Activation by Vesicles of Silicone Oil or Perfluorohexyloctane," Graefe's Archive for Clinical and Experimental Ophthalmology, 2005, 243, 345-358.
Lallemand et al., "Cyclosporine A delivery to the eye: a pharmaceutical challenge," European Journal of Pharmaceutics and Biopharmaceutics, 2003, 56(3):307-318, Abstract Only (1 page).
Lemp, M., "Management of Dry Eye Disease," The American Journal of Managed Care, 2008, 14 (3):S88-S101.
Lin, H. et al., "Dry eye disease: A review of diagnostic approaches and treatments," Saudi Journal of Ophthalmology, 2014, 28:173-181.
Mackiewicz, J. et al., "In Vivo Retinal Tolerance of Various Heavy Silicone Oils," Investigative Ophthalmology & Visual Science, 2007, 48 (4):1873-1883.
Matieucci et al., "Biocompatibility assessment of liquid artificial vitreous replacements: relevance of in vitro studies," Survey of Ophthalmology, 2007, 52(3):289-299, Abstract Only (1 page).
Meinert, H. et al., "Semifluorinated Alkanes—A New Class of Compounds with Outstanding Properties for Use in Ophthalmology," European Journal of Ophthalmology, 2000, 10(3), 189-197.
Meinert, H. et al., "The Use of Semifluorinated Alkanes in Blood-Substitutes," Biomaterials, Artificial Cells, and Immobilization Biotechnology, 1993, 21 (5):583-595.

Messmer, E.M., "The Pathophysiology, Diagnosis, and Treatment of Dry Eye Disease," (2015) Deutsches Arzteblatt International, 112(5):71-82.
Messmer et al., "Semifluorierte Alkane als Therapie bei Meibomdrüsen-Dysfunktion Ergebnisse einer prospektiven, multizentrischen Beobachtungsstudie", Presentation, DOG-Kongress, Sep. 29-Oct. 2, 2016, Berlin DOG (Deutsche Ophtalmologische Gesellschaft), Poster No. PSa03-02, 1 page (German language version).
Messmer et al., "Semifluorinated Alkanes as a Therapy for Meibomian Gland Dysfunction Results of a prospective, multi-centered observational study", Presentation, DOG-Kongress, Sep. 29, 2016-Oct. 2, 2016, Berlin DOG (Deutsche Ophtalmologische Gesellschaft), Poster No. PSa03-02, English Translation, 6 pages.
Messmer et al. "Semifluorinated Alkanes as a Therapy for Meibomian Gland Dysfunction Results of a prospective, multi-centered observational study", Presentation, DOG-Kongress, Sep. 29, 2016-Oct. 2, 2016, Berlin DOG (Deutsche Ophtalmologische Gesellschaft), Ophthalmologe, Aug. 2016 Poster No. PSa03-02, English Translation of Abstract, p. 138.
Murdan, S., "Enhancing the Nail Permeability of Topically Appied Drugs," Expert Opinion on Drug Delivery, 2008, 5 (11):1267-1282.
O'Rourke, M. et al., "Enhancing Delivery of Topical Ocular Drops," Cataract & Refractive Surgery Today Europe, 2016, 2 pages.
Perry, "Dry Eye Disease: Pathophysiology, Classification, and Diagnosis," The American Journal of Managed Care, 2008, 14(3):S79-S87.
Pflugfelder et al., "Treatment of Blepharitis: Recent Clinical Trials," 2014, 12(4):273-284, Abstract Only (2 pages).
Pflugfelder et al., "The Pathophysiology of Dry Eye Disease What We Know and Future Directions for Research," Ophthalmology (2017) 124(11 Supplement): S4-S13.
Pinarci, E. et al., "Intraocular Gas Application in the Diagnosis and Treatment of Valsalva Retiopathy in Case with Premacular Hemorrhage," XP002625604, Retina Vitreus, 2009, 17 (2):153-155, 1 page, abstract only.
Plassmann, M. et al., "Trace Analytical Methods for Semifluorinated n-Alkanes in Snow, Soil, and Air," Analytical Chemistry, 2010, 82(11):4551-4557.
Plassmann, M. et al., "Theoretical and Experimental Simulation of the Fate of Semifluorinated n-Alkanes During Snowmelt," Environmental Science & Technology, 2010, 44(17):6692-6697.
Rosca-Casian, O. et al., "Antifungal Activity of *Aloe vera* Leaves," Fitoterapia, 2007, 28, 219-222.
Rosenberg, A., "Effects of Protein Aggregates: An Immunologic Perspective," The AAPS Journal, 2006, 8 (3), E501-E507.
Sall, K. et al. "Two Multicenter, Randomized Studies of the Efficacy and Safety of Cyclosporine Ophthalmic Emulsion in Moderate to Severe Dry Eye Disease," Ophthalmology, 2000, 107(4):631-639.
Sato et al., "Vitrectomy and Intraocular Lens Implantation for Cytomegalovirus Retinitis in a Patient with Acquired Immunodeficiency Syndrome," Presented by Medical Online, New Ophthalmology, 1999, 16(7): 995-998 (4 pages).
Schmutz et al., "Fluorinated Vesicles Made from Combinations of Phospholipids and Semifluorinated Alkanes. Direct Experimental Evidence of the Location of the Semifluorinated Alkane within the Bilayer," Langmuir, 2003, 19:4889-4894.
Schnetler et al., "Lipid composition of human meibum: a review," S Afr Optom, 2013, 72(2), 86-93.
Spöler et al., "Towards a New in vitro Model of Dry Eye: The ex vivo Eye Irritation Test," Developments in Ophthalmology, 2010, 45, 93-107.
Steven, P. et al. "Semifluorinated Alkane Eye Drops for Treatment of Dry Eye Disease—A Prospective, Multicenter Noninterventional Study," Investigative Ophthalmology & Visual Science, 2015, 56:4493, Abstract Only (1 page).
Steven, P. et al. "Semifluorinated Alkane Eye Drops for Treatment of Dry Eye Disease—A Prospective, Multicenter Noninterventional Study" Journal of Ocular Pharmacology and Therapeutics, 2015, 31(8):498-503.
Steven et al., "Semifluorinated Alkane Eye Drops for Treatment of Dry Eye Disease Due to Meibomian Gland Disease," Journal of Ocular Pharmacology and Therapeutics, 2017, 33(9):1-8.

(56) References Cited

OTHER PUBLICATIONS

Stevenson, C., "Characterization of Protein and Peptide Stability and Solubility in Non-Aqueous Solvents," Current Pharmaceutical Biotechnology, 2000, 1, 165-182.
Tiffany, J.M., "Individual Variations in Human Meibomian Composition," Exp. Eye Res., 1978, 27, 289-300.
Troiano et al., "Effect of Hypotonic .4% Hyaluronic Acid Drops in Dry Eye Patients: A Cross-Study," Cornea 27(10): 1126-1130, 1 page (Abstract Only).
Wang, W., "Lyophilization and Development of Solid Protein Pharmaceuticals," International Journal of Pharmaceutics, 2000, 203, 1-60.
Wirta, David L. et al., "A Clinical Phase II Study to Assess Efficacy, Safety and Tolerability of Waterfree Cyclosporine Formulation for the Treatment of Dry Eye Disease," *Ophthalmology* 126:792-800 (2019).
"What is retinal vitrectomy?" Presented by: Medical Online, Obesity and Diabetes Mellitus, 2005, 4(2): 284-286 (3 pages).
Wong et al., "Perfluorocarbons and Semifluorinated Alkanes," Seminars in Ophthalmology; vol. 15 (1), 2000, p. 25-35.
Wu et al., "Physicochemical characterization and aerosol dispersion performance of organic solution advanced spray-dried cyclosporine A multifunctional particles for dry powder inhalation aerosol delivery," International Journal of Nanomedicine, 2013, 8:1269-1283.
Xalatan, Latanoprost Ophthalmic Solution, 50 μg/mL Prostaglandin $F_{2\alpha}$ analogue, Product Monograph, Jul. 21, 2014, 30 pages.
Zhang et al., "Surface micelles of semifluorinated alkanes in Langmuir-Blodgett monolayers," Phys. Chem. Chem. Phys., 2004, 6:1566-1569.
Agarwal et al., "Modern Approaches to the Ocular Delivery of Cyclosporine A," Drag Discovery Today, 2016, vol. 21, No. 6, pp. 977-988; doi: 10.1016/j.drudis.2016.04.002.
Agrahari et al., "A comprehensive insight on ocular pharmacokinetics," Drug Delivery and Translational Research, 2016, 6(6):735-754.
Al-Amri, et al., "Long-term use of 0.003% tacrolimus suspension for treatment of vernal keratoconjunctivitis," Oman Journal of Ophthalmology, 2017, 10(3):145-149.
Astellas Pharma US, Inc. (2019). PROGRAF(R); Highlights of Prescribing Information. Northbrook, IL: Astellas Pharma US, Inc.
Chaglasian et al., "Recycling Cyclosporine," Review of Cornea & Contact Lenses, 2016, 5 pages.
Chao, W. et al., "Report of the Inaugural Meeting of the TFOS i2 = initiating innovation Series: Targeting the Unmet Need for Dry Eye Treatment," (London, United Kingdom, Mar. 21, 2015) Accepted Manuscript, Accepted Date: Nov. 11, 2015, 94 pages.
Chen et al., "Persistent Inflammation Subverts Thrombospondin-1-Induced Regulation of Retinal Angiogenesis and Is Driven by CCR2 Ligation," The American Journal of Pathology, 2012, 180:235-245.
Dutescu et al., "Semifluorinated alkanes as a liquid drug earner system for topical ocular drug delivery," European Journal of Pharmaceutics and Biopharmaceutics, 2014, 88(1): 123-128.
Fischer, K.M., et al., "Effects of a topically applied 2% delta-9-tetrahydrocannabinol ophthalmic solution on intraocular pressure and aqueous humor flow rate in clinically normal dogs," American Journal of Veterinary Research, 2013, 74(2):275-280, Abstract Only (2 pages).
Galvao, et al., "Unexpected low-dose toxicity of the universal solvent DMSO," FASEB Journal, 2014, 28(3):1317-1330.
Gehisen, U. et al., "Omega-3 Fatty Acids Using F6H8-Carrier as Topical Therapy in Experimental Dry-Eye Disease," Investigative Ophthalmology & Visual Science, 2016, 57:417, Abstract Only (1 page).
German, E.J et al., "Reality of drop size from multi-dose eye drop bottles: is it cause for concern?" Eye, 1999, 13:93-100.
Goureau et al., "Increased nitric oxide production in endotoxin-induced uveitis. Reduction of uveitis by an inhibitor of nitric oxide synthase." The Journal of Immunology, 1995, 154(12): 6518-6523.
Grotenhermen, F., "Cannabinoids for therapeutic use—Designing systems to increase efficacy and reliability," American Journal of Drug Delivery, 2004, 2(4):229-240, Abstract Only (19 pages).
Kheirkhah, A., et al., "Topical 0.005% tacrolimus eye drop for refractory vernal keratoconjunctivitis," Eye (London, England), 2011, 25(7):872-880.
Moscovici, et al., "Clinical treatment of dry eye using 0.03% tacrolimus eye drops," Cornea, 2012, 31(8):945-949.
Murphy et al., "Cyclosporine vs Tacrolimus Therapy for Posterior and Intermediate Uveitis," Arch Ophthalmol. 2005, 123:634-641.
Novaliq GmbH Begins Phase II Clinical Trial of Cyclasol for the Treatment of Moderate to Severe Dry Eye Disease, (online), 5 pages, (2016); retrieved on Jan. 8, 2021 from the Internet: https://www.biospace.com/article/releases/novaliq-gmbh-begins-phase-ii-clinical-trial-of-cyclasol-for-the-treatment-of-moderate-to-severe-dry-eye-disease-/.
Ohashi, et al., "A randomized, placebo-controlled clinical trial of tacrolimus ophthalmic suspension 0.1% in severe allergic conjunctivitis," Journal of ocular pharmacology and therapeutics, 2010, 26(2):165-174.
Rosenbaum et al., "Contrasting Ocular Effects of Local versus Systemic Endotoxin," Investigative Ophthalmology & Visual Science, 2011, 52(9), 6472-6477.
Scherer et al., "Eyesol: A Novel Topical Ocular Drug Delivery System for Poorly Soluble Drugs," Drug Development & Delivery, 2013, vol. 13, No. 1, pp. 40-44.
Tamura et al., "Tacrolimus is a class II low-solubility high-permeability drug: The effect of P-glycoprotein efflux on regional permeability of tacrolimus in rats," Journal of Pharmaceutical Sciences, 2002, 91(3):719-729, Abstract Only (1 page).
Torkildsen et al., "A Clinical Phase 2 Study to Assess Safety, Efficacy, and Tolerability of CyclASol for the Treatment of Dry Eye Disease," Poster Presentation at AAO, 2017.
Xu et al., "A clinical grading system for retinal inflammation in the chronic model of experimental autoimmune uveoretinitis using digital fundus images," Experimental Eye Research, 2008, 87(4):319-326.
Yazu, et al., "The efficacy of 0.1% tacrolimus ophthalmic suspension in the treatment of severe atopic keratoconjunctivitis," Annals of allergy, asthma & immunology, 2019, 122(4):387-392.
Zeng, Y., "Atlas of Clinical Keratoconjunctival Disease," Hubei Science and Technology Press, 2011, 288-293.
Zeng, Y., "Atlas of Clinical Keratoconjunctival Disease," Hubei Science and Technology Press, 2011, English Translation, 287-299.

* cited by examiner

OPHTHALMIC COMPOSITIONS COMPRISING CICLOSPORIN

CROSS-REFERENCE TO RELATED APPLICATIONS

This application is a continuation application of U.S. application Ser. No. 16/336,005, filed on Mar. 22, 2019, which is a U.S. national stage application filed under 35 U.S.C. § 371 of International Application No. PCT/EP2017/074079, filed on Sep. 22, 2017, which claims priority to, and the benefit of, European Application No. 16190431.3, filed Sep. 23, 2016, the contents of each of which are incorporated herein by reference in their entireties.

BACKGROUND OF THE INVENTION

Ciclosporin is a challenging compound to formulate and to deliver due to its extremely poor solubility in water, and relatively large molecular size. Solubilizing excipients such as surfactants and organic or oil-based solvents are typically required in formulations of this compound.

Many ophthalmic formulations of ciclosporin disclosed in the art are based on oil-in-water emulsions in which the ciclosporin is dissolved in the oily phase (e.g. castor oil). One of the disadvantages of using organic or oil-based solvents or surfactants as a solubilizing agent in ophthalmic formulations is that these may often cause eye irritation such as pain, or stinging sensation when administered to the eye and may be poorly tolerated as a result. In the case of oily excipients, these may also have an inherent negative impact on vision (e.g. blurring) especially when present in substantial amounts, due to substantial differences in refractive index compared to that of physiological tear fluid. Oil-in-water emulsion formulations are also disadvantaged in that they may have limited drug load capacity, since while the active ingredient may have some solubility in the oil phase, this phase is only dispersed in the coherent aqueous phase, so that maximum overall drug concentration in the formulation is limited.

WO2011/073134A1 discloses pharmaceutical compositions in the form of solutions comprising ciclosporin and a semifluorinated alkane as a liquid vehicle which may be administered to the eye of a patient, such as for the treatment of keratoconjunctivitis. It is disclosed ciclosporin has a solubility of 2.54 g/L in the semifluorinated alkane 1-perfluorobutyl-pentane (F4H5) in the absence of any co-solvent. WO2011/073134A1 further teaches that with a small amount of ethanol as a co-solvent, the solubility of ciclosporin in F4H5 increases markedly, for example to 5.65 g/L when 1.0 wt % of ethanol is included in the composition. Ethanol is, generally speaking, not very tolerated by the human eye however it is mentioned that inclusion of a small amount of ethanol such as 1 wt % does not negatively affect tolerability. It would be an advantage, nevertheless, if the use of an additional further excipient and a co-solvent such as ethanol can be avoided.

It is thus an object of the present invention to provide improved compositions comprising ciclosporin which overcome these limitations of the prior art formulations. Further objects of the invention will be clear on the basis of the following description of the invention, examples and claims.

SUMMARY OF THE INVENTION

The invention provides a composition in the form of a clear solution comprising ciclosporin dissolved in 1-perfluorobutyl-pentane, wherein the composition is essentially free of a co-solvent and the concentration of ciclosporin is greater than about 2.6 mg/mL at 15-25° C., or greater than about 3.0 mg/mL. In a further aspect, the residual water content of the composition is less than about 0.04 mg/mL, or less than about 0.03 mg/mL.

In another aspect, the invention provides a composition in the form of a clear solution, comprising ciclosporin dissolved in 1-perfluorobutyl-pentane, wherein the composition is essentially free of a co-solvent, and wherein the composition has a residual water content of less than about 0.04 mg/ml, or less than about 0.03 mg/mL.

Preferably, the composition of the invention is essentially free of ethanol as a co-solvent. The composition is also preferably thermodynamically stable at 15-25° C.

Furthermore, the invention provides medical uses of these compositions, in particular for use for the treatment of keratoconjunctivitis sicca, meibomian gland dysfunction, or a symptom thereof. In one embodiment, these compositions are for ophthalmic use and are topically administered to the eye, such as in the form of eye drops.

In yet a further aspect, the invention provides for a composition that is obtainable by dissolving ciclosporin with a water content of less than about 1.6 wt %, or more preferably, by dissolving ciclosporin with a water content of less than about 1.0 wt %, based on the total weight of the ciclosporin, in 1-perfluorobutyl-pentane. A method of preparing a composition of the invention is also provided, the method comprising the steps of a) providing ciclosporin with a water content of less than about 1.6 wt %, or more preferably less than about 1.0 wt %, based on the total weight of the ciclosporin, and b) dissolving said ciclosporin in 1-perfluorobutyl-pentane.

DETAILED DESCRIPTION OF THE INVENTION

In a first aspect, the invention relates to a composition in the form of a clear solution comprising ciclosporin dissolved in 1-perfluorobutyl-pentane, wherein the composition is essentially free of a co-solvent and the concentration of ciclosporin, as determined at 15-25° C., is greater than about 2.6 mg/mL, or more preferably, greater than 3.0 mg/mL.

Ciclosporin (synonyms include cyclosporin A, CsA, or cyclosporine) is a cyclic nonribosomal peptide comprising 11 amino acids with the empirical formula $C_{62}H_{111}N_{11}O_{12}$ and molecular weight of 1202.61. It is an immunosuppressant drug that is widely used in post-allergenic organ transplant, to reduce the activity of the patient's immune system and thereby, the risk of organ rejection. Ciclosporin is typically provided as a colourless or white powder.

Preferably, the ciclosporin as used for the formulation of the composition and any of the embodiments or preferences as described herein has a water content of less than about 1.6 wt %, based on the total weight of ciclosporin. In another embodiment, the composition of the invention comprises of a total residual water content of less than about 0.04 mg/mL. More preferably, the ciclosporin as used for the formulation of the composition and any of the embodiments or preferences as described herein has a water content of less than about 1.0 wt %, based on the total weight of ciclosporin. In another embodiment, the composition of the invention comprises of a total residual water content of less than about 0.03 mg/mL. In yet a further embodiment, the composition comprises no residual water content.

The term residual water content as used herein refers to the fraction or trace amount of water that may be present in the composition originating from the composition components, such as ciclosporin and 1-perfluorobutyl-pentane.

The predominant contribution to residual water content in the composition can be attributed to water sorption or association with ciclosporin (e.g. not limited to, but for example derived from manufacturing process, or its transport and storage). Ciclosporin, as is usually available for medicinal use and formulation typically has a water content of about 1.6 wt % based on the weight of ciclosporin. The water solubility in 1-perfluorobutylpentane is on the other hand essentially negligible i.e. in very low amounts such as less than $1.20 \times 10^{-5}$ wt % based on weight of 1-perfluorobutylpentane.

The residual water content of ciclosporin, 1-perfluorobutyl-pentane, or of the composition of the invention comprising ciclosporin dissolved in 1-perfluorobutyl-pentane may be determined using methods and/or apparatus known in the art for moisture analysis, for example, but not limited to methods such as standard Karl-Fischer titration e.g. volumetric or coulometric.

It has been found that unexpectedly high concentrations of ciclosporin, such as greater than about 2.6 mg/mL, or more preferably greater than about 3.0 mg/mL at room temperature (i.e. 15-25° C.), may be dissolved in 1-perfluorobutyl-pentane without the need of a co-solvent. This has been observed in particular when the total residual water content of the compositions is less than about 0.04 mg/mL, in particularly less than 0.03 mg/mL, such as when the residual water content of ciclosporin is low.

While co-solvents may be useful as an aid for solubilizing ciclosporin and enable higher concentration formulations of ciclosporin to be obtained, it would be preferable if their use can be avoided. In particular, in context of ophthalmic use, co-solvents in the form of liquid solubilizing excipients such as surfactants or non-aqueous organic solvents may cause eye irritation or eye discomfort (e.g. blurred vision, or pain) when topically administered to the eye. Examples of co-solvents which may be used to help solubilize ciclosporin include oils such as glyceride or triglyceride oils (e.g. soybean oil, olive oil, sesame oil, cotton seed oil, castor oil or sweet almond oil), mineral oils (e.g. petrolatum or liquid paraffin), liquid oily fatty acids, fatty alcohols or sorbitol esters, or organic solvents e.g. glycerol, polyethylene glycol, propylene glycol or ethanol.

In a preferred embodiment, the composition of the invention is essentially free of a co-solvent such as defined above. As used herein, the term 'essentially free' means that there is no co-solvent in the composition, and if present then in trace or residual amounts such as to confer no technical advantage or relevance in respect of the object of the invention. Most preferably, the compositions as described herein are essentially free of ethanol as a co-solvent.

The absence of an organic co-solvent such as ethanol offers the advantages of a simpler two component formulation (essentially consisting of ciclosporin and 1-perfluorobutyl-pentane) as compared to a more complex three component formulation additionally comprising a co-solvent such as ethanol, in terms of factors such as cost, manufacturing, handling, packaging, and also patient compliance.

The higher concentrations of ciclosporin that may be obtained may offer advantages in terms of reducing the dosing frequency required by patients, and may also lead to more effective delivery of ciclosporin to the intended target tissue, for example to the eye. The compositions according to the invention may comprise of ciclosporin dissolved in 1-perfluorobutylpentane at a concentration of greater than about 2.6 mg/mL, as determined at room temperature or ambient temperature, i.e. about 15-25° C. In further embodiments, the concentration of ciclosporin in the composition at 15-25° C. is preferably greater than about 3.0 mg/mL, or may be in the range of from about 2.6 to 4.8 mg/mL, or 2.8 to 4.8 mg/mL, or preferably from about 3.0 to 4.8 mg/mL. In a further preferred embodiment, the concentration of dissolved ciclosporin is about 4.0 mg/mL as determined at 15-25° C. The concentration of ciclosporin dissolved in the solution may be quantified using methods known in the art, such as HPLC. As used herein, the term 'about' in reference or connection to a parameter such as the concentration, or concentration range of dissolved ciclosporin, or in relation to the residual water content of ciclosporin, based on the total weight of the ciclosporin, or in relation to the total residual water content in a composition according to the invention, may include the precise value as well as any value falling within the degree of variability usually observed in measuring or determining these parameters using the standard techniques and equipment known in the art and field.

In one embodiment, the ciclosporin as used herein is amorphous and is not crystalline or predominantly in any specific crystal form. Preferably, the ciclosporin that is dissolved in the 1-perfluorobutyl-pentane is obtained by a step of drying to reduce or to remove residual water from the ciclosporin. For example, the ciclosporin used in the preparation of a composition according to the invention, such as with a total residual water content of about 1.0%, is obtained by drying using drying methods known in the art such as drying under vacuum, drying in the presence of a desiccant or a drying agent.

A clear solution, as understood herein, refers to a liquid solution in which all solutes are fully dissolvable or dissolved under room temperature conditions i.e. between 15-25° C. The clear solution does not comprise of any particulate or solid phase components, for example undissolved ciclosporin and preferably has a refractive index approximate to that of water (i.e. 1.333) at room temperature. In one embodiment, the clear solution as presented by the composition of the invention may have a refractive index of between about 1.3 to 1.4.

In particular, the clear solution is thermodynamically stable between 15-25° C., meaning that under equilibrium, all of the dissolved components, including ciclosporin, remain in the dissolved state and that no phase separation, precipitation or changes to the physical form of the solution occurs. Preferably, the composition in the form of a clear solution according to the invention as described herein is thermodynamically stable when stored at 15-25° C. i.e. room temperature for a period of time such as at least about 2 weeks, or about 1 month, or 3 months, or at least about 6 months. Moreover, the invention may provide a composition which when stored at lower temperatures, such as under refrigeration, for example at temperatures between 0-10° C. may partially precipitate, but when brought back to 15-25°

C. (room temperature) returns to a thermodynamically stable and clear solution with all previously precipitated components dissolved again.

The liquid carrier of the composition according to the invention, 1-perfluorobutyl-pentane, is a semifluorinated alkane with the chemical formula $F(CF_2)_4(CH_2)_5H$. It is an inert, water-insoluble liquid, with a density of 1.284 g/cm$^3$ at 25° C. and refractive index of 1.3204 at 20° C. Alternative nomenclature for this compound includes F4H5, wherein F denote a linear perfluorinated alkane segment comprising 4 carbon atoms and wherein H denotes a linear and non-fluorinated alkane hydrocarbon segment of 5 carbon atoms.

The 1-perfluorobutyl-pentane as featured in any of the compositions or methods described herein is preferably essentially free of water. In such case, the presence of residual water in the composition according to the invention is derived from the ciclosporin or optionally, if present, one or more excipients that is functionally not a co-solvent. More preferably, the 1-perfluorobutyl-pentane does not comprise of any water, or has a water content of no more than the maximal solubility of water in 1-perfluorobutyl-pentane, for example, has a water-content of less than $1.6 \times 10^{-4}$ mg/mL as determined by methods known in the art for moisture analysis, such as Karl-Fischer titration methods.

In another aspect, the invention provides a composition in the form of a clear solution comprising ciclosporin dissolved in 1-perfluorobutyl-pentane, wherein the composition is essentially free of a co-solvent, and wherein the composition has a residual water content of less than about 0.04 mg/ml.

In a further embodiment, the invention provides a composition in the form of a clear solution comprising ciclosporin dissolved in 1-perfluorobutyl-pentane, wherein the composition is essentially free of a co-solvent, and wherein the composition has a residual water content of less than about 0.03 mg/ml.

In further embodiments, the composition may have a total residual water content of less than 0.03 mg/mL or of less than 0.025 mg/mL, or of less than 0.02 mg/mL, or of less than 0.015 mg/mL, or less than 0.01 mg/mL.

In particular, the relative ratio of ciclosporin to residual water content as featured in the compositions as described in any of the embodiments and featured herein may be at least greater than about 65 to 1, or preferably, greater than 100 to 1, or greater than 200 to 1.

The concentration of ciclosporin in such compositions at 15-25° C. is preferably from about 0.5 to 4.8 mg/mL. In further embodiments, the concentration of ciclosporin as determined at room temperature of the composition may be in the range of from about 2.6 to 4.8 mg/mL, or preferably from about 3.0 to 4.8 mg/mL. In a particularly further preferred embodiment, the concentration of dissolved ciclosporin at 15-25° C. is about 4.0 mg/mL. Lower concentrations of ciclosporin, such as from about 0.5 to 2.6 mg/mL, or from the range of about 0.5 to 1.0 mg/mL of ciclosporin dissolved in 1-perfluorobutyl-pentane may also contemplated in for the invention. Due to the dependence of solubility in relation to temperature, there is general tendency for active ingredients such as ciclosporin to precipitate out of solution when the solution is stored at lower temperature conditions. The low water content of the ciclosporin such as described for the invention advantageously may provide improved physical stability to the solution formed in 1-perfluorobutylpentane, for example even when the solution is stored at lower temperatures, such as under refrigeration (e.g. at 0-10° C.), any precipitation that may occur will easily dissolve again when the composition is brought back to 15-25° C. (room temperature).

In yet a further embodiment, the composition as described in any of the embodiments or preferences featured herein, including any combinations thereof, consists essentially of 1-perfluorobutyl-pentane and ciclosporin and has a residual water content in an amount of less than about 0.04 mg/mL.

In yet another embodiment, the composition as described in any of the embodiments or preferences featured herein, including any combinations thereof, consists essentially of 1-perfluorobutyl-pentane and ciclosporin and has a residual water content in an amount of less than about 0.03 mg/mL.

The residual water content of the composition may be primarily attributed to the residual water content of ciclosporin, for example, wherein at least 99% of the residual water content of the composition can be attributed to ciclosporin. As used herein, the term "consists" and related terms "consisting" or "consist" is to be understood as meaning that no other features, other than those prefaced by the term are present. The term 'essentially' means if present then in trace or residual amounts such as to confer no technical advantage or relevance in respect of the object of the invention.

The composition as described in any of the above embodiments, and embodiments herein, including any combinations or preferences thereof, may be used as a medicine, and for therapeutic use. The use of said compositions in the manufacture of a medicament or medicine for the treatment of a patient in need thereof is also provided for in the context of the present invention.

Particular preferred is the use of the composition for the treatment of keratoconjunctivitis sicca, or a symptom thereof. Keratoconjunctivitis sicca is also known as dry eye disease or syndrome, or dysfunctional tear syndrome. A patient having keratoconjunctivitis sicca may experience any one of, or a combination of tear hyperosmolarity, tear film instability or abnormalities in the lipid layer composition of the tear film. Aqueous-deficient dry eye disease, evaporative dry eye disease, Sjögren syndrome, lacrimal gland insufficiency, meibomian gland dysfunction as understood herein may be considered to be within the scope, for example as sub-types, of keratoconjunctivitis sicca.

Symptoms of keratoconjunctivitis may include any one, or combination of the following: a dry, scratchy, gritty, or sandy feeling in the eye; foreign body sensation; pain or soreness; stinging or burning; itching; increased blinking; eye fatigue; photophobia; blurry vision; redness; mucus discharge; contact lens intolerance; excessive reflex tearing. It is understood that not all patients suffering from keratoconjunctivitis sicca may exhibit all symptoms simultaneously. Hence, there is currently no uniform set of criteria for diagnosing the disease. It is however important to note that, within the scope of the present invention, any of the aspects, symptoms or pathophysiological consequences of keratoconjunctivitis sicca may be addressed.

Also preferred is the use of the composition as defined in any of the embodiments described herein for the treatment of meibomian gland dysfunction, or a symptom thereof. Meibomian gland dysfunction may be characterized by gland obstruction and clogging through hyperkeratinisation of the gland and increased viscosity of the meibum lipid secretions of the meibomian gland ducts. The quantitative or qualitative secretion of the lipid components required for the tear film may be altered in the case of patients with meibomian gland dysfunction. This may lead to a failure in forming a stable and continuous tear film, which may be further followed by evaporative loss and hyperosmolarity.

Meibomian gland dysfunction can arise from a primary lid-margin related disease or a secondary disease arising from systemic disorders such as acne rosacea, or seborrheic dermatitis. In addition to any one of the symptoms as described for keratoconjunctivitis sicca as described above, patients with meibomian gland dysfunction may also experience symptoms including any one or combination thereof, of itching, redness, swelling, pain or soreness, discharge accumulation or crusting at the eye lid margins.

The compositions according to the above uses are preferably ophthalmic compositions that are topically administered to the surface of the eye and to any such region or tissue of the eye that may be accessible to topical administration, such as to the cornea or conjunctiva.

The compositions of the invention as described herein may be provided as part of a kit, for example a kit comprising the composition and a container adapted for holding the composition, wherein the container has a dispensing means adapted for topical administration of the composition to the eye or ophthalmic tissue. Optionally, such kit may comprise a water-desiccant or water-desiccating means to safeguard a stable residual water content, for example during storage. An increase in residual water content may the affect solubility of ciclosporin which in turn may affect the stability of the composition and may result in precipitation. Further optionally, instructions for use of the kit in the treatment of keratoconjunctivitis sicca or a symptom thereof, or for use of the kit in the treatment of meibomian gland dysfunction or a symptom thereof may also be included as part of the kit.

In another aspect of the invention, the invention provides for a composition obtainable by dissolving ciclosporin with a water content of less than about 1.6 wt %, based on the total weight of ciclosporin, in 1-perfluorobutyl-pentane. In yet another aspect of the invention, the invention provides for a composition obtainable by dissolving ciclosporin with a water content of less than about 1.0 wt %, based on the total weight of ciclosporin, in 1-perfluorobutyl-pentane. The ciclosporin used for obtaining such compositions may in other embodiments have a water content of less than about 0.8 wt %, or 0.6 wt % or 0.5 wt % or 0.4 wt %, or 0.3 wt %. Particularly preferred is the use of ciclosporin with a water content of 0.4 wt % or less, based on the weight of ciclosporin to obtain a solution in 1-perfluorobutyl-pentane, preferably a clear solution.

Preferably, the composition, including any of its embodiments or preferences as described above is obtained wherein the ciclosporin is dissolved in 1-perfluorobutyl-pentane in the absence of a co-solvent, for example in the absence of ethanol or any of the co-solvents mentioned above. The concentration of ciclosporin that may be dissolved at 15-25° C. to obtain the composition is preferably greater than 2.6 mg/mL. In further embodiments, composition obtained may have a concentration of ciclosporin at 15-25° C. greater than 3.0 mg/mL, or in the range of from about 2.6 to 4.8 mg/mL, or preferably from about 3.0 to 4.8 mg/mL. In a further preferred embodiment, the concentration of dissolved ciclosporin is about 4.0 mg/mL.

Preferably, the composition obtained, including any of its embodiments or preferences as described above provides a clear solution that is thermodynamically stable at 15-25° C.

The composition obtainable according to any of the above embodiments, may be used as a medicament, or used for the manufacture of a medicament. In particular, the composition may be used for use in the treatment of keratoconjunctivitis sicca or a symptom thereof; or for use in the treatment of meibomian gland dysfunction or a symptom thereof. Preferably, the compositions obtainable according to any of the embodiments described herein are ophthalmic compositions, and are used for topical administration to the surface of the eye and to any such region or tissue of the eye that may be accessible to topical administration, such as to the cornea or conjunctiva.

The invention further provides a method of preparing a composition as described in any of the above embodiments or preferences comprising the steps of a) providing ciclosporin with a water content of less than about 1.6 wt % based on the total weight of the ciclosporin, and b) dissolving said ciclosporin in 1-perfluorobutyl-pentane.

Further embodiments of this method may include a method of preparing compositions according to the following embodiments:

1. A composition in the form of a clear solution comprising ciclosporin dissolved in 1-perfluorobutyl-pentane, wherein the composition is essentially free of a co-solvent and the concentration of ciclosporin at 15-25° C. is greater than about 2.6 mg/mL.

2. The composition according to item 1, wherein the residual water content of the composition is less than about 0.04 mg/mL.

3. The composition according to any of items 1 or 2, wherein the concentration of ciclosporin at 15-25° C. is in the range of from about 2.6 to 4.8 mg/mL, or preferably from about 3.0 to 4.8 mg/mL.

4. A composition in the form of a clear solution comprising ciclosporin dissolved in 1-perfluorobutyl-pentane, wherein the composition is essentially free of a co-solvent, and wherein the composition has a residual water content of less than about 0.04 mg/mL.

5. The composition according to item 4, wherein the concentration of ciclosporin at 15-25° C. is from about 0.5 to 4.8 mg/mL.

6. The composition according any of items 1 to 5, wherein the co-solvent is ethanol.

7. The composition according to any of items 1-6, wherein the solution is thermodynamically stable at 15-25° C.

The invention moreover further provides a method of preparing a composition as described in any of the above embodiments or preferences, namely, a method of preparing a composition in the form of a clear solution comprising ciclosporin dissolved in 1-perfluorobutyl-pentane, and wherein the composition is essentially free of a co-solvent, the method comprising the steps of a) providing ciclosporin with a water content of less than about 1.0 wt % based on the total weight of the ciclosporin, and b) dissolving said ciclosporin in 1-perfluorobutyl-pentane.

In a further embodiment, step a) may be the provision of ciclosporin having a water content of less than about 0.8 wt %, or 0.7 wt %, or 0.6 wt %, or 0.5 wt % or preferably 0.4 wt % based on the weight of ciclosporin. In another embodiment, step a) may be the provision of ciclosporin having a water content of less than about 0.3 wt %, based on the weight of ciclosporin.

In yet further embodiments, the method as described above may be for preparing the following compositions:

1. A composition in the form of a clear solution comprising ciclosporin dissolved in 1-perfluorobutyl-pentane, wherein the composition is essentially free of a co-solvent, wherein the concentration of ciclosporin at 15-25° C. is from about 0.5 to 4.8 mg/mL, or more preferably about 0.5 to 3.0 mg/mL, or about 0.5 to 1.0 mg/mL.

2. A composition in the form of a clear solution comprising ciclosporin dissolved in 1-perfluorobutyl-pentane, wherein the composition is essentially free of a co-solvent, wherein the concentration of ciclosporin at 15-25° C. is in the range of from about 3.0 to 4.8 mg/mL.

3. The composition according to any of item 1 or 2, wherein the co-solvent is ethanol.

4. The composition according to any of items 1 to 3, wherein the solution is thermodynamically stable at 15-25° C.

Moreover, step a) of the method may comprise drying ciclosporin with a water content of about 1.6 wt % or greater than about 1.6 wt % based on the total weight of the ciclosporin.

The step of providing a ciclosporin with low residual water content, such as providing ciclosporin with a water content of less than about 1.0 wt % based on the total weight of the ciclosporin, may include a step of drying ciclosporin which has a higher water content, such as greater than 1.6 wt % based on the total weight of the ciclosporin, or greater than about 1.3 wt %, or about 1.4 wt % or about 1.5 wt %, based on the total weight of the ciclosporin.

In particular, the step of providing ciclosporin having a water content of less than about 1.0 wt %, 0.8 wt %, or 0.6 wt %, or preferably 0.4 wt % may include a step subjecting ciclosporin with a higher water content, preferably ciclosporin with a water content of about 1.6 wt %, or greater than 1.6 wt % based on the total weight of the ciclosporin, to a drying process. Methods of drying include, but are not limited to, drying the ciclosporin under vacuum, optionally in the presence of a water-desiccant or drying agent. The duration, and method of drying may be adapted in order to provide the targeted water content value of ciclosporin.

Further embodiments of the invention may be as follows:

1. A composition in the form of a clear solution comprising ciclosporin dissolved in 1-perfluorobutyl-pentane, wherein the composition is essentially free of a co-solvent, and wherein the composition has a residual water content of less than about 0.03 mg/mL.

2. The composition according to item 1, wherein the concentration of ciclosporin at 15-25° C. is from about 0.5 to 4.8 mg/mL.

3. The composition according to any preceding item 1 or 2, wherein the co-solvent is ethanol. 7.

4. The composition according to any preceding item, wherein the solution is thermodynamically stable at 15-25° C.

5. A composition according to any of the preceding items for use as a medicine.

6. The composition for use according to item 5, wherein the composition for use in the treatment of keratoconjunctivitis sicca or a symptom thereof; or for use in the treatment of meibomian gland dysfunction or a symptom thereof.

The following examples serve to illustrate the invention however these are not to be understood as restricting the scope of the invention.

EXAMPLES

Example 1

Isothermal sorption calorimetry of ciclosporin at 25° C. was determined using a 28 mm two-chamber calorimetric cell inserted in a double-twin microcalorimeter. A dry sample, prepared by drying ciclosporin for one day under vacuum and over molecular sieves was placed in the upper (sorption) chamber and pure water was injected in the lower (vaporization) chamber. The water activity was calculated from the power of evaporated water registered in the vaporization chamber. It was found that ciclosporin may comprise of up to about 8 wt % water when exposed to a relative humidity of 99% RH.

Figure 1:
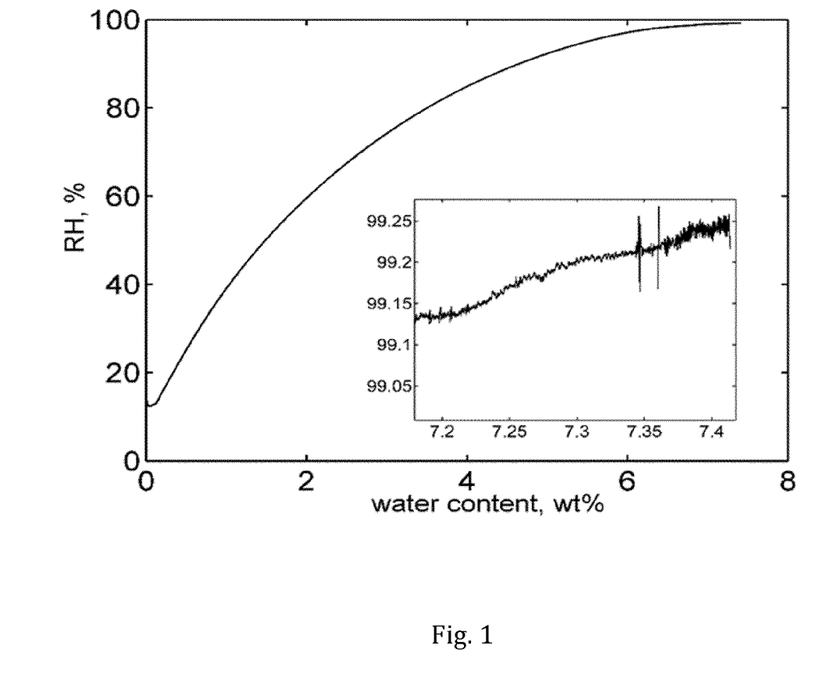
FIG. 1 depicts the water sorption of ciclosporin obtained from sorption calorimetry at 25° C. The inset is a zoomed area of the ciclosporin sorption isotherm at the higher relative humidity (RH) levels.

FIG. 1 depicts the water sorption of ciclosporin obtained in sorption calorimetry at 25° C. The inset in the FIG. 1 is a zoomed area of the ciclosporin sorption isotherm at higher relative humidity (RH) levels. The water content of ciclosporin at 99.25% RH is approximately 7.41 wt %.

The solubility of ciclosporin in 1-perfluorobutyl-pentane was then determined as a function of its water content. Samples, dried as above were incubated for 5 days in desiccators at different fixed relative humidity at room temperature. The various relative humidity was regulated in the desiccators using saturated salt solutions (LiCl, $MgCl_2$, $Mg(NO_3)_2$, NaCl, $K_2SO_4$).

After incubation, excess ciclosporin of each sample were added to 1-perfluorobutyl-pentane and each sample was sealed and incubated for 3 days at constant agitation and temperature (room temperature) using an orbital shaker (IKA KS130 Basic, IKA®-Werke GmbH & Co). The resulting saturated solutions were filtered through a 0.2 µm PTFE syringe filter and diluted with acetonitrile (dilution factor of 50, 100 or 200) prior to determination of concentration by reversed phase HPLC-UV. The concentration of ciclosporin was calculated from calibration curves of standard solutions (10-100 µg/mL) prepared in acetonitrile. Based on the water sorption isotherm for ciclosporin, the solubility of ciclosporin in 1-perfluorobutyl-pentane as a function of the water content of ciclosporin could be determined. Table 1 depicts the dataset obtained.

TABLE 1

| Relative Humidity (RH) % | Water content, wt % | CsA solubility in F4H5 (mg/mL) |
|---|---|---|
| 0 | 0.00 | 4.75 ± 0.025 |
| 11 | 0.40 | 3.88 ± 0.027 |
| 33 | 0.76 | 2.75 ± 0.167 |
| 52 | 1.57 | 2.64 ± 0.099 |
| 53 | 1.60 | 2.00 ± 0.099 |
| 75 | 3.05 | 1.10 ± 0.061 |
| 97 | 6.00 | 0.90 ± 0.073 |
| 100 | n.a. | 0.52 ± 0.021 |

Figure 2A:
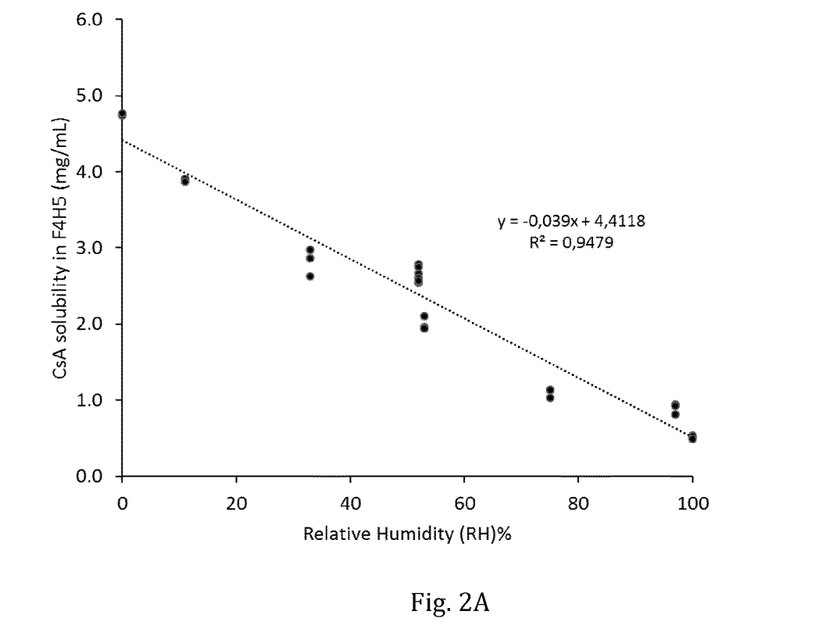
FIG. 2A depicts the solubility of ciclosporin in 1-perfluorobutyl-pentane as a function of relative humidity.
Figure 2B:
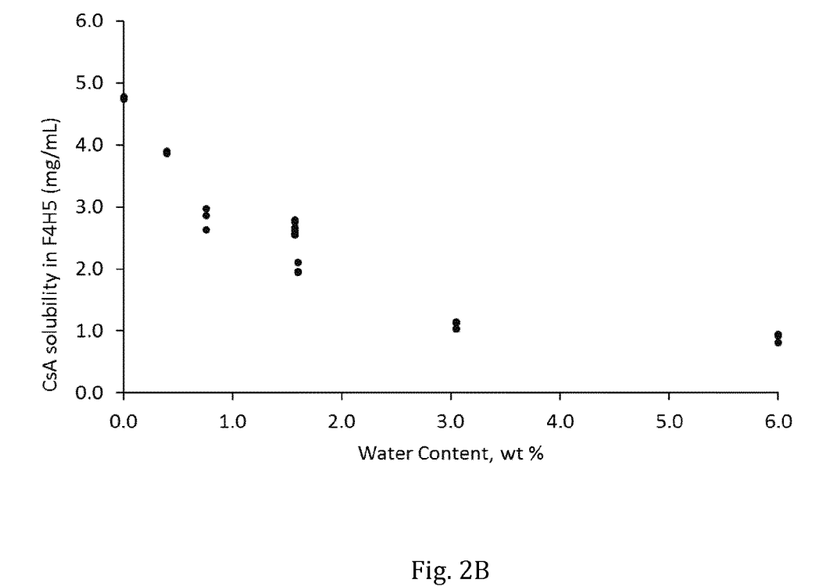
FIG. 2B depicts the solubility of ciclosporin in 1-perfluorobutyl-pentane as a function of water content of the ciclosporin.

FIG. 2A depicts the solubility of ciclosporin in 1-perfluorobutyl-pentane as a function of relative humidity and FIG. 2B depicts the solubility of ciclosporin in 1-perfluorobutyl-pentane as a function of water content in the ciclosporin. It was observed that ciclosporin solubility in 1-perfluorobutyl-pentane starts to rapidly increase from when the water content residue in the ciclosporin is less than 1.6 wt % based on the total weight of the ciclosporin (FIG. 2B).

Karl-Fischer titration measurements of ciclosporin prior to the drying procedure (i.e. not treated) and after drying (i.e. for one day under vacuum and in the presence of molecular sieves, as described above) were also obtained, and maximal solubility in 1-perfluorobutyl-pentane were analogously determined. The results are summarized in Table 2.

TABLE 2

| Ciclosporin | CsA Water content (wt %) | Residual water content in CsA-F4H5 composition[1] (mg/mL) | CsA Solubility in F4H5 (mg/ml) |
| --- | --- | --- | --- |
| As supplied | 1.56 ± 0.06 | 0.0412 | 2.64 ± 0.10 |
| Dried | 0.40 | 0.0163 | 4.08 ± 0.39 |

[1]Values expressed excluding the negligible residual water in F4H5 of <1.6 × $10^{-4}$ mg/mL.

Significantly higher concentrations, i.e. greater than about 2.6 mg/mL, and up to 4.8 mg/mL of ciclosporin dissolved in 1-perfluorobutyl-pentane can be obtained when ciclosporin with a low and reduced water-content, such as less than about 1.6 wt %, and in particular less than 1.0 wt % is used. An approximately 1.6-fold unexpected increase in solubility of the ciclosporin in 1-perfluorobutyl-pentane was observed using ciclosporin with a reduced water content, of about 0.4 wt % based on the weight of the ciclosporin.

The invention claimed is:

1. A composition in the form of a clear solution comprising ciclosporin dissolved in 1-perfluorobutyl-pentane, wherein the composition is essentially free of a co-solvent, and wherein the composition has a residual water content of less than about 0.03 mg/mL, and wherein the ciclosporin has a water content of less than about 1.0 wt.% based on the total weight of the ciclosporin.

2. A method for the preparation of a composition according to claim 1, the method comprising the steps of a) providing ciclosporin with a water content of less than about 1.0 wt % based on the total weight of the ciclosporin, and b) dissolving said ciclosporin in 1-perfluorobutyl-pentane.

3. The method according to claim 2, wherein step a) of providing ciclosporin with a water content of less than about 1.0 wt% based on the total weight of ciclosporin, comprises a step of drying ciclosporin with a water content of about 1.6 wt %, or greater than about 1.6 wt % based on the total weight of the ciclosporin.

4. A pharmaceutical kit, comprising:
(i.) a composition according to claim 1;
(ii.) a container adapted for holding the composition, wherein the container has a dispensing means adapted for topical administration of the composition to the eye or ophthalmic tissue;
(iii.) optionally, a water-desiccant; and
(iv.) optionally, instructions for use of the kit in the treatment of kerato-conjunctivitis sicca or a symptom thereof, or for use of the kit in the treatment of meibomian gland dysfunction or a symptom thereof.

5. The composition according to claim 1, wherein the composition consists of ciclosporin and 1-perfluorobutyl-pentane.

6. The composition according to claim 1, wherein the relative ratio of ciclosporin water content to the residual water content of the composition is greater than about 65 to 1.

7. A method for treating a patient, the method comprising a step of administering a composition according to claim 1 to a patient in need thereof.

8. The method of treatment according to claim 7, wherein the composition is administered to a patient having kerato-conjunctivitis sicca or a symptom thereof, or meibomian gland dysfunction or a symptom thereof.

9. The method of treatment according to claim 8, wherein the symptom of keratoconjunctivitis sicca is selected from dry, scratchy, gritty, or sandy feeling in the eye; foreign body sensation; pain or soreness; stinging or burning; itching; increased blinking; eye fatigue; photophobia; blurry vision; redness; mucus discharge; contact lens intolerance; excessive reflex tearing and any combinations thereof.

10. The method of treatment according to claim 8, wherein the symptom of meibomian gland dysfunction is selected from itching, redness, swelling, pain or soreness, discharge accumulation or crusting at the eye lid margins and any combinations thereof.

11. The method of treatment according to claim 7, wherein the composition is topically administered to the surface of the eye or to any region or tissue of the eye accessible to topical administration.

12. The method of treatment according to claim 7, wherein the composition consists essentially of 1-perfluorobutyl-pentane and ciclosporin.

13. The method of treatment according to claim 7, wherein the concentration of ciclosporin in the composition at 15-25° C. is from about 0.5 to 4.8 mg/mL.

14. The method of treatment according to claim 11, wherein the composition is topically administered to the cornea or conjunctiva.

* * * * *